United States Patent [19]

Ranawat et al.

[11] Patent Number: 4,778,475
[45] Date of Patent: Oct. 18, 1988

[54] FEMORAL PROSTHESIS FOR TOTAL HIP REPLACEMENT

[75] Inventors: Chitranjan S. Ranawat, Alpine, N.J.; Albert H. Burstein, Stamford, Conn.; Donald L. Bartel, Freeville, N.Y.

[73] Assignee: New York Society for the Relief of the Ruptured and Crippled, New York, N.Y.

[21] Appl. No.: 120,737

[22] Filed: Nov. 10, 1987

Related U.S. Application Data

[63] Continuation of Ser. No. 852,440, Apr. 15, 1986, abandoned.

[51] Int. Cl.$^4$ .............................................. A61F 2/32
[52] U.S. Cl. .................................................... 623/23
[58] Field of Search ...................... 623/16, 18, 20, 22, 623/23

[56] References Cited

U.S. PATENT DOCUMENTS 4,536,894 8/1985 Galante et al. ...................... 623/18
4,589,883 5/1986 Kenna ................................. 623/22

Primary Examiner—Richard J. Apley
Assistant Examiner—David J. Isabella
Attorney, Agent, or Firm—Brumbaugh, Graves, Donohue & Raymond

[57] ABSTRACT

A femoral component for a hip joint prosthesis comprises a proximal portion adapted to be received in the intertrochanteric region of a femur, a neck portion extending obliquely medially, anteriorly and superiorly from the proximal portion and adapted to be joined to a femoral head element, and a stem portion smoothly merging with and extending inferiorly from the proximal portion. The proximal portion has anterior and prosterior aspects that converge medially and inferiorly and intersect a rounded medial aspect oriented obliquely to the stem portion both anteriorly and medially, said aspects defining a generally wedge-shaped body adapted to engage the endosteal surfaces of the femur in the intertrochanteric region such that substantially all loads are transmitted from the component to the bone in the intertrochanteric region and load transfers through other surfaces are minimized.

3 Claims, 3 Drawing Sheets

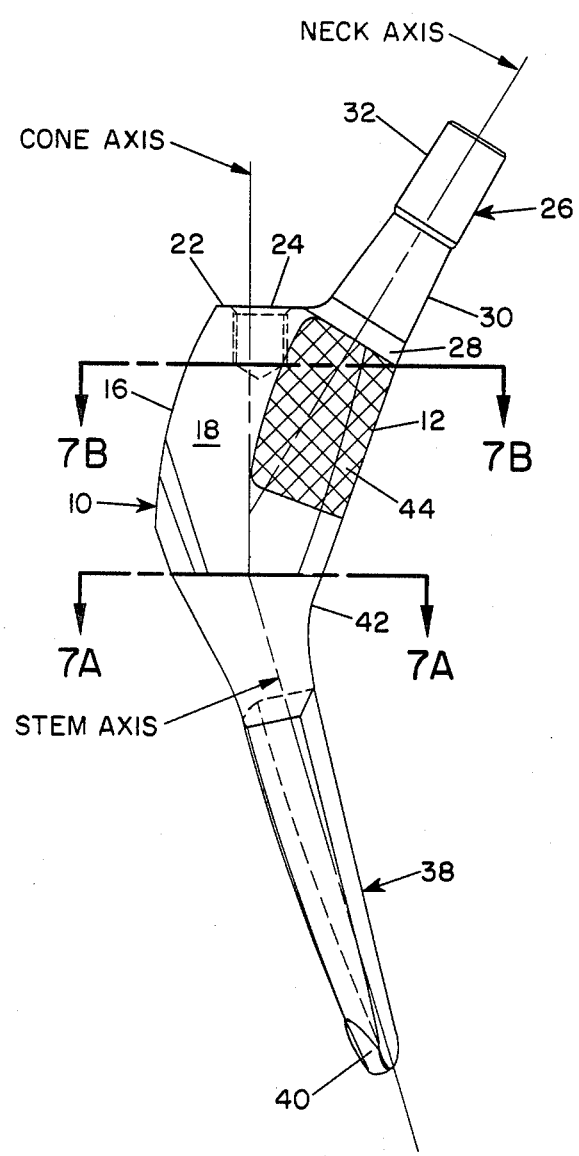
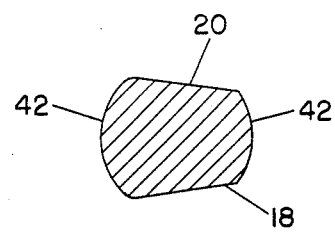
FIG. 7A
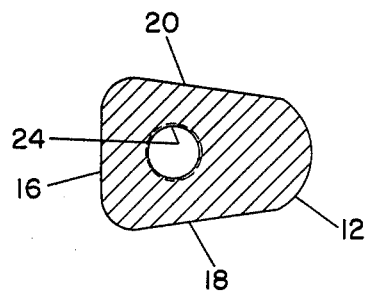
FIG. 7B
FIG. 7

FEMORAL PROSTHESIS FOR TOTAL HIP REPLACEMENT

This application is a continuation of application Ser. No. 852,440, filed on 4/15/86 now abandoned.

BACKGROUND OF THE INVENTION

In total hip replacement the head and most of the neck of the proximal femur are removed and a femoral prosthesis is implanted. The conventional approach in designing a femoral prosthesis has assumed that loads should be transferred between the prosthesis and the femur over the entire length of the part of the prosthesis that is received within the femur, which includes, of course, the stem that extends a relatively large distance into the femoral shaft. The distribution of the load transfer depends on the specific design of the prosthesis and the type of fixation.

In prostheses that are implanted with bone cement (polymethyl methacrylate), the loads are transferred from the prosthesis through the cement to the endosteal surface of the bone throughout the entire cement layer, but the distribution of stress is non-uniform, though it can be predicted using stress analysis techniques such as the finite element method. In prostheses that are implanted without bone cement, sintered porous metal coatings on the prosthesis promote ingrowth of bone for biological retention, and the distribution of the load transfer from the prosthesis to the endosteal surface of the bone depends upon the apposition of the bone, the extent of bone ingrowth and the design of the prosthesis. In presently known designs of non-cemented femoral prostheses the apposition and, hence, the regions where load transfer will occur are unpredictable.

Bone remodels according to the loads applied to it, and the long term stress distribution in the bone is, therefore, of great importance. A beneficial effect of the remodeling property of bone is, of course, that the structural characteristics of regions of the bone that are loaded by the prosthesis and by the tendons at the hip joint are likely to be enhanced. Conversely, regions of the bone where the loads are decreased deteriorate through loss of bone structure. It is, therefore, important that a prosthesis provide for load transfer that is predictable and that minimizes the possibility of unloading of the bone.

Inherent in known designs of femoral hip joint prostheses of both the cemented and non-cemented types is some degree of unloading of the bone in the region of the stem of the prosthesis, inasmuch as the stem is coupled to the bone to a lesser or greater extent, depending on the design. When the bone bends, the stem has to bend, which produces stress in the stem, stress (load) that would otherwise be borne by the bone. Bending of the stem also alters the load transfer between the bone and the prosthesis at the proximal region, tending to unload the proximal medial aspect of the femur, a region where the bone is usually under a large axial compressive load, and load the proximal lateral aspect, a region where the bone is under tension. Bone resorption at the proximal femur reduces load transfer in that region and increases the load transfer in the stem. Loosening of the implant and stem fracture can result.

SUMMARY OF THE INVENTION

The present invention is a femoral prosthesis for total hip replacement that fulfulls three main objectives. First, it provides loading in the intertrochanteric region of the femur that produces stress levels similar to those occuring in a normal anatomical femur. Second, it provides predictable load transfer by establishing specific, known regions of contact between the prosthesis and endosteal surfaces of the femur and minimizing contact other than in those regions. Third, transfer of loads between the stem and bone in the axial direction is minimized so that the proximal portion of the femoral shaft continues to be loaded in approximately the same region as it is in a normal anatomical hip joint. The foregoing principles ensure to a maximum degree possible that the prosthesis will distribute loads to the femur in a manner that will preserve bone structure. In addition it is intended that stresses in the stem of the prosthesis be minimized.

A femoral component, according to the present invention, is adapted to be implanted in the proximal portion of a femur for biological retention without cement and has a proximal portion adapted to be received in the intertrochanteric region of the femur, a neck portion extending superiorly from the proximal portion obliquely both medially and anteriorly and adapted to be joined to a femoral head element, and a stem portion smoothly merging with and extending inferiorly from the proximal portion. The invention is characterized in that the proximal portion has anterior and posterior aspects that converge both medially and inferiorly and intersect a rounded medial aspect oriented obliquely to the stem portion both anteriorly and medially, said aspects defining a generally wedge-shaped body adapted to engage the endosteal surfaces of the femur in the intertrochanteric region of the femur such that substantially all loads are transmitted from the component to the bone in that region and load transfers through other surfaces, especially the stem, are minimized.

In a preferred embodiment the anterior and posterior aspects of the proximal portion are planar surfaces, and a recess extends continuously along the medial portions of the anterior and posterior aspects and around the medial aspect, the recess containing a porous medium adapted to accept bone ingrowth at the calcar region of the femur for biological retention.

For a better understanding of the invention, reference may be made to the following description of an exemplary embodiment, taken in conjunction with the accompanying drawings.

DESCRIPTION OF THE DRAWINGS

FIG. 7 is a front elevational view taken orthogonally to a plane defined by the axes of the neck and cone, as indicated by the arrowed lines 7—7 adjacent FIG. 6; and FIGS. 1A, 1B, 1C, 7A and 7B are cross-sectional views taken along planes represented by the correspondingly labelled, arrowed lines in the FIGS. 1 and 7 and in the direction of the arrows.

DESCRIPTION OF THE EMBODIMENT

The drawings show a component for a right hip. The unique design of the invention requires individual right and left parts, unlike many designs, in which a single part can be used in either hip.

Figure 6:
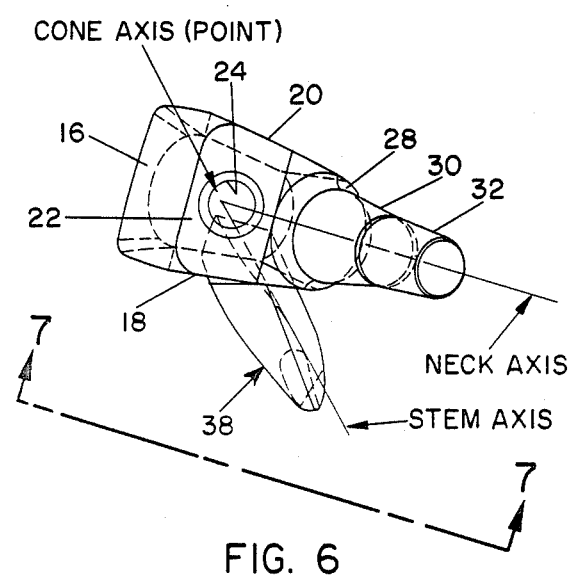
FIG. 6 is a top plan view looking down the cone axis.

For purposes of computer-assisted design and computer-assisted manufacture (CAD-CAM) of the embodiment, the proximal portion 10 of the embodiment is based on a cone having an axis ("cone axis") and a cone angle or taper established by the medial extremity of a curved (radiused) medial aspect 12 of the proximal portion (see FIGS. 7, 7A and 7B). Apart from the medial extremity, which is an element of the imaginary cone, and a vestigial conical surface 14 at the inferior, lateral extremity, the proximal portion 10 bears little resemblance to a cone. The superior lateral aspect 16 of the proximal portion is a segment of a cylindrical surface generated by a line rotated about an axis located medially of the component and perpendicular to a plane defined by the neck and cone axes (see FIG. 7). The anterior and posterior aspects 18 and 20 of the proximal portion 10 are planar and lie symmetrically with respect to the cone axis and converge both medially and inferiorly (see FIGS. 6, 7D and 7E). Hence, the proximal portion is a wedge-shaped body having a narrower end (the medial aspect 16) presented medially and somewhat inferiorly. The lateral portion 22 of the superior surface is flat and perpendicular to the cone axis. A threaded hole 24 opening at the surface 22 accepts an instrument used for inserting as well as for extracting the component, should revision of the hip replacement ever be required.

A neck portion 26 extends superiorly and obliquely both medially and anteriorly from the medial part of the proximal portion, beginning at a radiused and blended juncture 28 with the proximal portion 10, continuing along a conical part 30 and terminating in a Morse-type taper 32 that can accept a femoral head element (not shown) of a desired size and length driven home on the taper 32.

Figure 1:
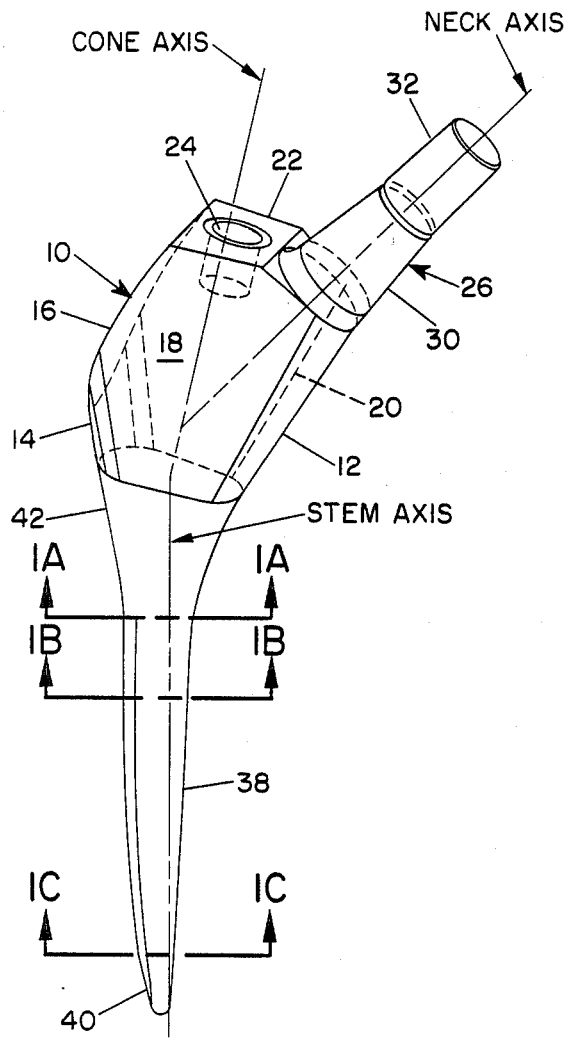
FIG. 1 is a front elevational view of the embodiment taken orthogonally to a medial-lateral plane of the prosthesis that includes the stem axis.
Figure 3:
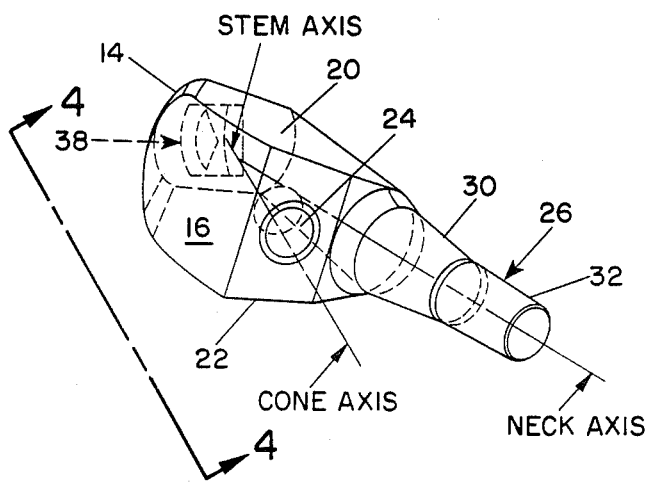
FIG. 3 is a top plan view looking directly down the stem axis.
Figure 1A:
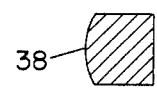
Figure 1B:
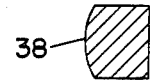
Figure 1C:
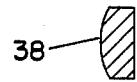
Figure 2:
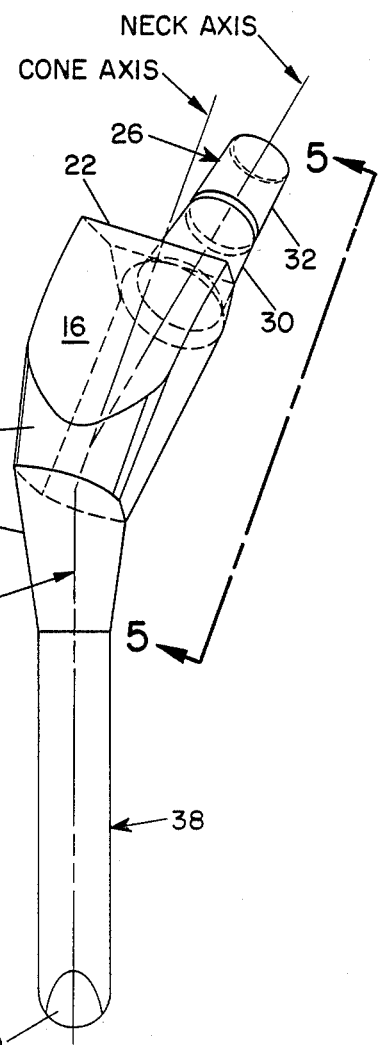
FIG. 2 is a side elevational view of the lateral side taken orthogonally to an anterior-posterior plane that includes the stem axis.
Figure 4:
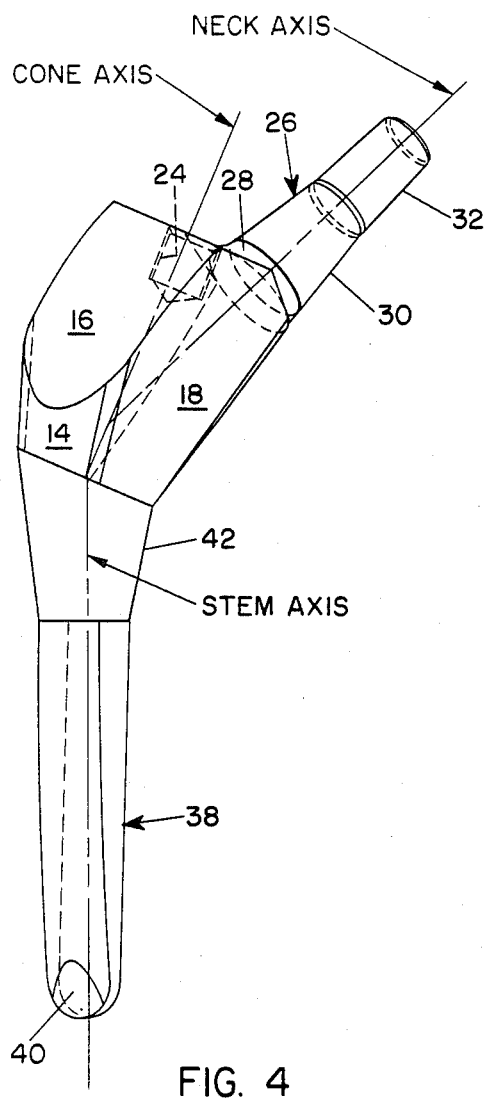
FIG. 4 is a front elevational view taken orthogonally to a plane defined by the axes of the stem and the proximal portion ("cone"), as indicated by the arrowed lines 4—4 adjacent FIG. 3.
Figure 5:
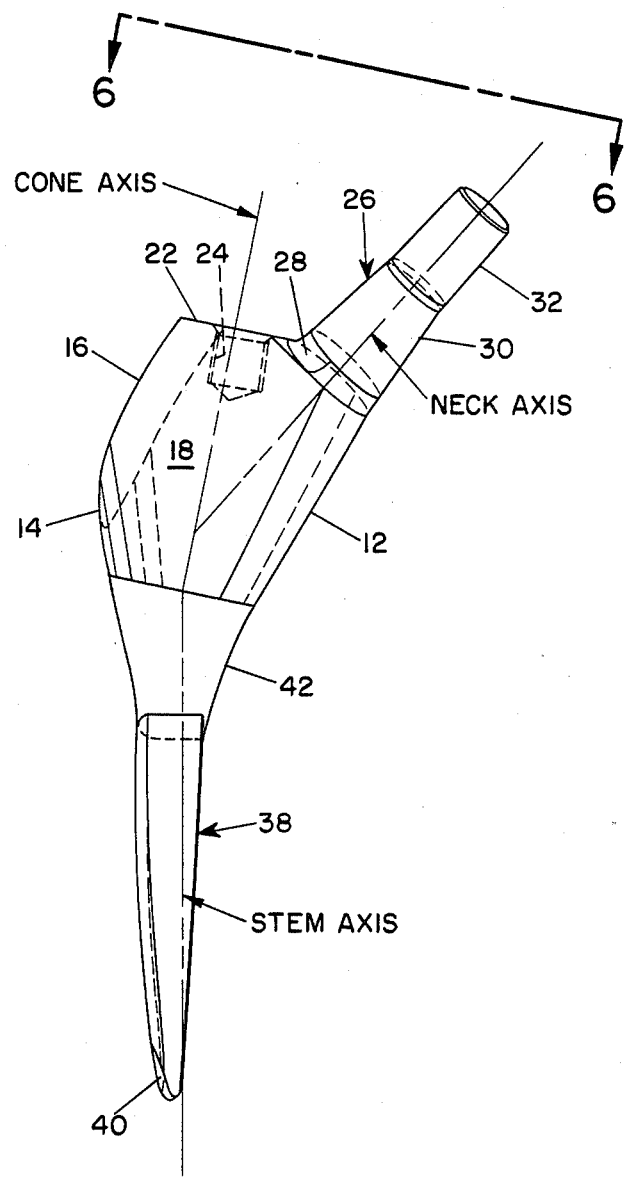
FIG. 5 is an elevational view taken orthogonally to a medial-lateral plane that includes the cone axis, as indicated by the arrowed lines 5—5 adjacent FIG. 2.

A stem portion 38 extends inferiorly from the proximal portion. The stem axis is oblique at a large obtuse included angle (about 160 degrees) to the cone axis (FIG. 4). It tapers inferiorly to a slender distal tip 40 from a smoothly blended juncture 42 with the proximal portion 10.

The cross-hatching in FIG. 7 represents a recess 44 that extends continuously along approximately the medial one-half of the anterior and posterior aspects 18 and 20 and across the medial aspect 12 of the proximal portion 10. The recess contains a porous medium capable of accepting an ingrowth of bone for biological retention. The technology of porous materials is known per se in the art from, for example, Morscher, E. (ed.), *The Cementless Fixation of Hip Endoprostheses.* New York, Springer-Verlag, 1983, and Engh, C. A., Bobyn, J. D., *Biological Fixation in Total Hip Arthroplasty,* Thorofare, N.J., Slack, Inc., 1985. The configuration of the prosthesis of the present invention does not depend on bone ingrowth for stability, but ingrowth should occur and enhance stability.

The preferred material for the implant is titanium alloy, Ti-6Al-4V, and the porous medium is sintered titanium beads in a recess 0.040 inch deep to a thickness of 0.050 inch plus or minus 0.010 inch.

The femur is prepared for reception of the implant by first reaming the femoral canal and then broaching the proximal part of the femur with a broach that is properly undersized for slight interference between the proximal portion of the component and the broached endosteal surface of the cortical bone in the region of the calcar. Except for being slightly undersize, the shape of the broached portion exactly matches the shape of the wedge-like body of the proximal portion of the prosthesis. The broaching instruments include a guide that provides for straight-line broaching along an axis corresponding to the cone axis of the component. In this respect, also, the cone axis has significance (beyond CAD-CAM, as mentioned), notwithstanding only minimal existence of actual conical surfaces in the proximal portion.

In the prosthetic joint the medial, anterior and posterior aspects of the proximal portion 10 of the femoral prothesis, according to the invention, transmit a compressive load into the proximal medial portion of the femur in the region of the calcar, where the bone is thick, strong, and heavily loaded in compression is a normal anatomical hip. When the femur bends, lateral loads may be transmitted to the lateral distal aspect of the stem portion, causing the stem to be bent and stressed. Axial stresses in the bone, however, are not transferred to the stem, so the bone is not relieved from axial loads and should retain its structural integrity. The tension loads in the femur in the region of the greater trochanter are also little affected by the prosthesis. Apart from the lateral distal tip the stem and the region generally corresponding to the porous-coated recess, load transfer from the prosthesis to the bone is minimized.

We claim:

1. A femoral component for a hip joint prosthesis adapted to be implanted in the proximal portion of a femur for biological retention without a cement comprising a proximal portion adapted to be received in the intertrochanteric region of a femur, a neck portion extending obliquely medially, anteriorly and superiorly from the proximal portion and adapted to be joined to a femoral head element, and an elongated stem portion defining a longitudinal axis and smoothly merging with and extending inferiorly from the proximal portion, the proximal portion having a medial aspect that is a segment of a conical surface having a cone axis disposed obliquely both anteriorly and medially to the longitudinal axis and anterior and posterior aspects that are planar surfaces that converge medially and inferiorly and are disposed symmetrically with respect to the cone axis and the medial aspect, said anterior, posterior and medial aspects defining a generally wedge-shaped body adapted to engage the endosteal surfaces of the proximal medial portion of the femur in the intertrochanteric region such that compressive loads are transmitted from the component to the bone in the intertrochanteric region and load transfers through other surfaces are minimized.

2. A component according to claim 1 and further characterized in that there is a recess extending continuously along the medial portions of the anterior and posterior aspects and across the medial aspect, and the recess contains a porous medium adapted to accept bone ingrowth at the calcar region of the femur for biological retention.

3. A component according to claim 1 wherein a part of the lateral aspect of the proximal portion adjacent the juncture of the proximal portion with the stem portion is a conical surface having as its axis the cone axis.

* * * * *